United States Patent [19]

Davis et al.

[11] 3,932,541

[45] Jan. 13, 1976

[54] PROCESS FOR THE PREPARATION OF BROMINATED PENTAERYTHRITOLS

[75] Inventors: Ralph A. Davis, Midland; Ronald G. Tigner, Coleman; Joseph J. Pedjac, Mount Pleasant; Laurence I. Peterson, Midland, all of Mich.

[73] Assignee: The Dow Chemical Company, Midland, Mich.

[22] Filed: May 24, 1973

[21] Appl. No.: 363,687

Related U.S. Application Data

[63] Continuation-in-part of Ser. No. 171,334, Aug. 12, 1971, abandoned.

[52] U.S. Cl.............. 260/633; 260/488 J; 260/333; 260/654 R
[51] Int. Cl.$^2$........................................ C07C 31/34
[58] Field of Search...................................... 260/633

[56] References Cited
FOREIGN PATENTS OR APPLICATIONS

| 3,927,230 | 11/1964 | Japan | 260/633 |
|---|---|---|---|
| 764,664 | 12/1956 | United Kingdom | 260/633 |
| 935,362 | 11/1955 | Germany | 260/633 |

OTHER PUBLICATIONS

Zelinsky et al. Ber. 46 (1913) 163–164.
Geiseler et al., Z. Naturforsch 22A (1967) 1511–1516.

*Primary Examiner*—Howard T. Mars
*Attorney, Agent, or Firm*—Ralph M. Mellom

[57] ABSTRACT

Brominated pentaerythritols are prepared at reaction temperatures of from about 85° to 135°C. by reacting pentaerythritol with HBr in the liquid phase employing a solvent medium containing from about 0.8 to about 25 mole percent of an aliphatic carboxylic acid of 2 to 8 carbon atoms and their anhydrides, based on the pentaerythritol. The HBr is fed continuously to the reactor throughout the reaction. The water formed as a result of the reaction remains in the reaction mixture until substantial completion of the reaction. The product can be predominantly dibromoneopentyl glycol or tribromoneopentyl alcohol and is characterized by the absence of tar formation.

9 Claims, No Drawings

PROCESS FOR THE PREPARATION OF BROMINATED PENTAERYTHRITOLS

CROSS-REFERENCE TO RELATED APPLICATION

This application is a continuation-in-part of our earlier application, Ser. No. 171,334, filed Aug. 12, 1971, now abandoned.

BACKGROUND OF THE INVENTION

The preparation of brominated pentaerythritols has been carried out by reacting fuming hydrobromic acid with pentaerythritol at temperatures of 120° to 160°C. for periods of 8–15 hours and by reacting hydrogen bromide with pentaerythritol in glacial acetic acid; see Berlow, Barth and Snow, *The Pentaerythritols*, ACS Monograph No. 136, pp. 99–100. In the reactions with hydrobromic acid, long reaction times and high temperatures are required. Reactions carried out in glacial acetic acid form large amounts of undesirable acetate by-product; moreover, in the prior art processes large amounts of tar are formed, and where such formation is obviated, it is obtained at the expense of having to use extremely high pressures.

Thus, Conia et al., Bull. Soc. Chim. France, 1961, p. 1803, discloses a process whereby pentaerythritol and HBr are reacted using acetic acid in large amounts as a solvent. This process produces an unknown mixture of brominated neopentyl acetates which have to be hydrolyzed back to the alcohols, stripped and distilled. The yield or products are not revealed. The melting point of this unknown product is 90°–95°C. which is neither that of tribromoneopentyl alcohol (72°C.) nor dibromoneopentyl glycol (110°C.).

Bincer et al., Ber. 61 B (1928), p. 542, discloses the reaction of pentaerythritol with aqueous HBr using no catalyst at 140°C. for 20 hours. Using elevated pressures, they obtain a 44% tribromoneopentyl alcohol yield which is exemplified by a dark color.

Zelinsky, Ber. 46 (1913), pp. 163–164, also reacts pentaerythritol with aqueous HBr in the absence of a catalyst and obtains at 44% yield. He uses a sealed system under pressure and obtains a "very dark" product.

In the somewhat related processes whereby pentaerythritol chlorohydrins are formed, processes are disclosed where either large amounts of acetate by-products are formed necessitating saponification, unduly and undesirable high pressures are used in the process, and/or the products are replete with tar formation, necessitating distillation. In the bromination of pentaerythritols, saponification of the reaction product to reduce acetate content is not feasible because the rate of decomposition of the brominated pentaepythritol is greater than the rate of saponification. Consequently, the oxetane is formed, plus irreversible lachrymatory (2-bromomethyl-3-bromo-propene) as well as other undesirable by-products.

Thus, British Pat. No. 764,664 discloses a process for preparing pentaerythritol trichlorohydrin by reacting pentaerythritol with at least 3 moles and preferably 5 to 10 moles of hydrogen chloride at extremely high pressures and temperatures between 150° and 200°C. in the presence of at least 10 mole percent of an aliphatic monocarboxylic acid or ester of same per each mole of pentaerythritol. An inert organic solvent may be used. All the ingredients are combined at the outset of the reaction and reacted in a silver-plated autoclave. Saponification is used in all cases to transform the monoacetate formed into free trichlorohydrin. At the lower range of acetic acid used, the yield is only 63%. This process has the disadvantage that it must be reacted at elevated temperatures and pressures. As indicated in U.S. Pat. No. 3,217,045, the British Pat. No. 764,664 process has little to recommend it. In Column 1, lines 30–39 of the cited U.S. patent, reference is made to the British patent's German equivalent patent specification (No. 955,233). It is there stated that "this process does not proceed in the manner specified unless elevated pressures are applied. The process is difficult to carry out on a commercial scale on account of the aqueous hydrochloric acid which forms during the reaction . . ." Likewise, Japanese Pat. No. 39-27230 points out that the process of British Pat. No. 764,664 requires the use of pressure equipment and presents problems in operation and recovery of the product.

Japanese Pat. No. 39-27230 discloses the manufacture of pentaerythritol trichlorohydrin through a direct chlorination of pentaerythritol with HCl gas with a small amount of acetic anhydride. This process teaches the use of 3 to 50 mole equivalents of acetic anhydride at 170°–200°C. to react HCl gas with pentaerythritol. It obviates the use of high pressures in the reaction; however, because they remove the water that is formed during the reaction continuously throughout the reaction by passing large excesses of HCl to sweep it out, the Japanese obtain large amounts of tar formation at low levels of acetic anhydride. Consequently they teach that the preferred range of acetic anhydride is 25 to 50 mole equivalents. This corresponds to a 50 to 100 mole percent of carboxylic radical per mole equivalent of pentaerythriol. The Japanese patent indicates that at low levels of acetic anhydride, yield is drastically reduced and etherization (tar formation) becomes more prominent than chlorination. As will be shown below, at the levels of acetic acid used in the instant invention, the Japanese process produces about 1 pound of tar per 1 pound of usable product. Finally, the Japanese state that acetic acid cannot be used as a catalyst.

These significant drawbacks to the preparation of brominated pentaerythritols have led to an extensive search for methods of avoiding these problems.

SUMMARY OF THE INVENTION

It has now been discovered according to the present invention that in the preparation of brominated pentaerythritols by reacting pentaerythritol with HBr, the process and the final products are greatly improved by conducting the reaction in the liquid phase at a temperature of from about 85° to about 135°C. in an inert solvent containing as a catalyst an aliphatic monocarboxylic acid of from 2 to 8 carbon atoms or its anhydride, having a concentration of from about 0.8 to about 25 mole percent per mole of pentaerythritol, by feeding the HBr to the reactor containing the pentaerythritol and solvent continuously throughout the reaction while not removing the water from the reaction mixture until the reaction is substantially complete.

The products of the invention are brominated pentaerythritols where 1 to 3 of the hydroxyls have been replaced by bromine. Optionally, the products of the invention may contain some chlorine provided that the starting pentaerythritol is a chlorinated derivative. Preferred products, however, contain only bromine as the halogen atoms.

A special advantage of the process of the present invention is that essentially any product distribution of brominated pentaerythritols, i.e., the mono-, di-, or tribromopentaerythritol, can be obtained with substantially no tar being produced. Accordingly, the product can be used directly without further purification in most, if not in all, applications. As used herein, monobromopentaerythritol designates pentaerythritol where 1 hydroxyl has been replaced by bromine, dibromoneopentyl glycol designates pentaerythritol where 2 hydroxyls are replaced by bromine and tribromoneopentyl alcohol is pentaerythritol where 3 hydroxyls are replaced by bromine. Brominated pentaerythritols refer to any one or combination of these three compounds.

In this method of preparing brominated pentaerythritols, the primary and essential feature of the invention is conducting the reaction in a solvent medium containing a catalytic amount of an aliphatic carboxylic acid or its anhydride in such a manner that the HBr is fed to the reactor continuously throughout the reaction while the water that is formed during the reaction plus that used as a solvent, if any, remains in the reaction mixture until substantial completion of the reaction. By feeding HBr continuously to the reactor throughout the reaction is meant saturating the reaction mixture with HBr so as to push the reaction towards production of the desired predominant product. If the reaction is run under pressure higher than atmospheric, the HBr is fed at a rate consistent with maintaining the desired pressure and temperature throughout the reaction. If run at atmospheric pressure, the HBr feed is at a rate which insures saturation throughout the reaction period with, for practical reasons, a minimal venting of HBr. The lower concentration of the acid or anhydride is essentially that concentration that will catalyze the reaction. The upper limit on the concentration is not critical so long as the ester formed in the reaction is maintained at a low level. In the preferred practice of the present invention, considering the anhydride as the free acid, the solvent medium contains a carboxylic acid concentration of about 0.8 to about 25 mole percent based on the pentaerythritol charged. Of even greater interest because of the very desirable reaction obtained with a minimum amount of ester by-products is a concentration of about 2 to about 10 mole percent per mole of pentaerythritol charged.

The carboxylic acids useful in the present invention are preferably aliphatic monocarboxylic acids or halogenated aliphatic monocarboxylic acids of 2 to about 8 carbon atoms and their anhydrides. Especially preferred are those acids of 2 to about 4 carbons, with acetic acid being of special interest because of its low cost and desirable effectiveness.

Although the use of a catalytic amount of a carboxylic acid or its anhydride to catalyze the reaction along with the continual feed of the HBr and the concomitant nonremoval of water during the reaction is the focal point of the present invention, the presence of an inert solvent is also important. Reaction of anhydrous HBr with pentaerythritol in the absence of a solvent produces a black resinous mass and only small amounts of the desired product. Consequently, the presence of a solvent is important.

Even though the presence of a solvent is essential, the nature of the solvent does not appear to be critical except that the solvent should not substantially react with the pentaerythritol or HBr under the conditions employed in the process. Representative examples of preferred solvents include: water; saturated hydrocarbon solvents such as benzene, toluene, xylene, cyclohexane, petroleum ether and heptane; and halogenated hydrocarbon solvents such as perchloroethylene, trichloroethylene, chlorobenzene, dichlorobenzene, hexachlorocyclopentadiene, ethylene dibromide, methylene chloride and methylenedibromide. This definition specifically excludes carboxylic acid solvents for they would react with the pentaerythritol to form esters.

With respect to the other properties of the solvent, those which provide a reaction mixture having a reflux temperature within the desired reaction temperatures are preferred. Of greatest interest because of their effectiveness and low cost are perchloroethylene and water. Of course, any of the solvents may be used alone or in combination with each other.

The reactants in the process of the present invention are well known. Usually the reaction is between pentaerythritol and HBr, but in some reactions in the invention, pentaerythriol having 1 or 2 hydroxyls replaced by chlorine or bromine may be employed. Of course, monobromopentaerythritol and dibromoneopentyl glycol are brominated as intermediates in the reaction. HBr is generally added to the reaction in anhydrous form, but the aqueous acid may be used.

The ratio of reactants employed in the present invention is essentially a function of the desired product. Usually a stoichiometric excess of HBr based on the desired product is employed to assure completion of the reaction, with an excess of about 20 to 50 percent being sufficient to obtain the desired product in predominant yield.

The temperature of the reaction may vary widely so long as the halogen replacement occurs. In the preferred practice of the invention, it has been found that reaction temperatures of about 85° to about 135°C. are desirably employed, with temperatures of 90° to 120°C. being preferred because of the particularly good reaction and product obtained.

Normally, the reaction is run at atmospheric or superatmospheric pressure. Although this variable is not critical, atmospheric to about 75 p.s.i.g. is desirable because in this range, special high-pressure equipment is not necessary. Under the conditions of the process of this invention, such pressures can be effectively utilized without the creation of tar. The reaction time, of course, depends on the many factors in the invention, but in normal practice, the reaction is conveniently carried out in substantially less than 6 hours for the preparation of the dibromoneopentyl glycol and less than 15 hours for tribromoneopentyl alcohol.

In the manufacture of brominated pentaerythritols, it is desirable that the brominated pentaerythritol product is in a form immediately useful as a fire retardant agent in such areas as unsaturated polyester resins and polyurethane foams. To meet this requirement, the process must produce a product that is low in color. By low in color is meant less than about 100 APHA for the dibromoneopentyl glycol product and less than about 200 APHA for the tribromoneopentyl alcohol. Moreover, the process itself must be operable at atmospheric pressure or superatmospheric pressure of a range not requiring special equipment; no elaborate purification processes should be involved; the process must generate only minimal waste streams; the process must be simple to operate and employ standard chemical processing equipment; the process must be able to use a minimal excess of hydrogen bromide; and finally the process must be one that gives high yields of the brominated pentaerythritol products and minimal etherification type by-products. The process of the present invention meets the above criteria in all ways.

SPECIFIC EMBODIMENTS

Example 1 — Preparation of Tribromoneopentyl Alcohol

To a 50-gallon reactor equipped with a high speed agitator, a reflux condenser and a pressure regulator, was charged 5 parts by weight of acetic acid, 227 parts of pentaerythritol and 236 parts of perchloroethylene. Anhydrous HBr (510 parts) was added continuously over a period of 12 hours at the maximum rate so as to maintain the temperature of 110° to 120°C. and a pressure of 10 to 18 p.s.i.g. This amount of HBr was about a 20% excess over the stoichiometric amount required to obtain tribromoneopentyl alcohol. After the addition of HBr, the reactor was maintained under the reaction conditions for 30 minutes. The reaction mixture was then distilled to remove the HBr as an azeotrope with the perchloroethylene and the water that was formed as a result of the reaction until the final conditions of 110° and 25 mm. of Hg were attained. The product was treated with 200 ml. of epichlorohydrin to obtain an off-white solid having an APHA color of 90 (20 g. product/100 ml. methanol). An acetylated sample of the product was analyzed to G.L.C. and found to contain 0.2% dibromoneopentyl moiety and 99.8% tribromoneopentyl moiety by weight. A G.L.C. analysis of a nonacetylacted sample showed that 4.2 mole percent of the product was an acetate moiety.

Example 2 — Preparation of Dibromoneopentyl Glycol

Using a 100-gallon glass lined reactor equipped with an agitator, a 4 inch by 10 foot glass column (no packing), a 13 foot square condenser, a 10-gallon glass lined receiver and a 2-stage jet for vacuum, 390 pounds of perchloroethylene, 10 pounds of acetic acid (0.167 pound moles), and 450 pounds of pentaerythritol (3.31 pound moles) were charged to the reactor. This amounted to 2.2 weight percent or 5 mole percent of acetic acid based on pentaerythritol. The temperature was raised to 105°C. and 685 pounds of anhydrous HBr (8.45 pound moles) was fed into the reactor at the maximum rate while holding the temperature at 105° to 112°C. and the pressure at 5 to 20 p.s.i.g. This amount of HBr was in 27% excess of the stoichiometric amount needed to produce dibromoneopentyl glycol. The HBr was added in 4 hours and 45 minutes and the reaction mixture was stirred for an additional 30 minutes at 110°C. The HBr, water and perchloroethylene was then stripped off at 110°C. at 25 mm. After stripping, the reactor was blanketed with nitrogen and sampled. 1200 ml. of epichlorohydrin were added to neutralize the remaining acid and the product allowed to stir for 20 minutes at 100°C.

The liquid product was then fed to a flaker and 865 pounds of white (APHA of 35), flaked product (about 99% of the expected yield based on pentaerythritol) having the following analysis was recovered:

monobromopentaerythritol — 6.0 weight percent
dibromoneopentyl glycol — 82.3 weight percent
tribromoneopentyl alcohol — 11.7 weight percent

Example 3 Preparation of Brominated Pentacerythritols With Concomitant Removal of Water Throughout The Reaction This example was carried out to determine the effect of removing the water from the hydrobromination of pentaerythritol. The reaction was carried out under substantially anhydrous conditions. Removal of water by azeotropic distillation during and throughout the reaction is taught in U.S. Pat. Nos. 2,763,679, 3,118,003, 3,217,045 and Japanese Pat. No. 39-27230. The processes disclosed in these patents are directed to the preparation of chlorinated pentaerythritols, and the HCl—$H_2O$ azeotrope is swept out in these processes by the use of a large excess of HCl. To effect the removal of the water formed during the course of the reaction in a hydrobromination, an inert organic solvent was used to lower the azeotroping temperature. Further, large excesses of anhydrous hydrogen bromide were passed through the reaction mixture to facilitate the removal of the water in the same manner as the cited patented processes use large excesses of HCl.

A 2-liter resin flask equipped with a mechanical stirrer, gas dispersion tube, thermocouple, and a steam heated partial condenser was connected through the condenser to a Dean-Stark tube, a water cooled reflux condenser and a water filled acid trap. Anhydrous hydrogen bromide was metered to the reactor through a Rotometer and entered the reaction mixture at the bottom of the flask via the fritted gas dispersion tube. The reactor was charged with 544 g. (4 moles) of pentaerythritol, 24 g. (0.4 mole or 10 mole percent) of acetic acid, 200 ml. of 62% aqueous HBr (2.7 mole HBr) and 200 ml. of o-xylene. The reaction mixture was then heated to 80°C. and anhydrous HBr passed in at a rate such that the gas passed through the system and into the water filled acid trap at about 6.8 g./min. The reaction temperature was held at about 117°C. After 1 hour and 7 minutes, about 5.6 moles of anhydrous HBr had been passed into the mixture in addition to the 2.7 moles of HBr present initially. In that time, 50 ml. of aqueous acid was collected in the Dean-Stark tube. The reaction mixture was sampled and found to have a composition containing about 3.0 weight percent pentaerythritol, 61.6% monobromopentaerythritol, 35.1% dibromoneopentyl glycol, and 0.5% tribromoneopentyl alcohol. The APHA color of the stripped product was found to be 440. In all cases, the APHA color was determined by taking a 20 g. of product and dissolving it in 100 ml. of methanol. The HBr feed was stopped and the reaction cooled to room temperature under a nitrogen blanket overnight. In the morning the mixture was reheated and the HBr gas sparge continued so that excess HBr was continually vented from the system. After 2 hours a total of 10.6 moles of HBr had been passed into the reactor, making a total of HBr of 13.3 moles. Upon sampling the brominated pentaerythritol reaction product, it was found to consist of about 6.9 weight percent monobromopentaerythritol, 78.4 weight percent dibromoneopentyl glycol, and 14.8% tribromoneopentyl alcohol. The APHA color of the stripped product was about 2800. Approximately 95 ml. of aqueous acid had been collected in the Dean-Stark tube. The reaction was continued until 99% of the pentaerythritol moiety was tribrom-. The total reaction time was about 31 hours run in approximate 8-hour segments and cooled between segments. The total HBr passed into the reactor including that originally present was 31.1 moles and the stripped product was a black, crystalline solid having a APHA color of about 11,000. About 410 ml. of aqueous acid containing 4.6 moles of HBr was drained from the Dean-Stark tube during the run and approximately 85% of the theoretical water was collected in the Dean-Stark tube.

This example showed that when the water is removed during the reaction as contrasted with the process of the present invention, unacceptable tar formation results. This formation occurs rapidly as shown by the first analytical sample which had an APHA of about 440 after 1 hour of reaction time.

While the reaction was run in 8-hour segments, the use of this technique did not significantly contribute to the color formation as the reaction temperature was allowed to drop to room temperature during each period in which the HBr feed was stopped.

Example 4 — Hydrochlorination of Pentaerythritol

To show that the azeotroping of the water formed during the reaction was as detrimental in hydrochlorination as taught in the prior art as it is in hydrobromination of pentaerythritol, pentaerythritol was hydrochlorinated in the manner specified by Japanese Pat. No. 39-27230. Example 2 of that patent was carried out as follows: To 136 g. of pentaerythritol, 25.5 g. (0.25 mole equivalent on pentaerythritol) of acetic anhydride was added and the mixture was gradually heated to dissolve the ingredients while dry hydrogen chloride gas was passed through the mixture. The chlorination by hydrogen chloride gas was continued for 10 hours at 180°–185°C. Hydrogen chloride gas was introduced to the reactor from the bottom and the water produced was recovered from the top section as a hydrochloric acid solution. At the end of the reaction and distillation, 97 g. of residue with a boiling point of 105°–121°C./2 mm. Hg was obtained. Analysis of this residue indicated that 64.4% of this product was pentaerythritol trichlorohydrin and 35.2% monoacetate.

It was noted that the reaction mixture was initially nearly colorless but rapidly turned a light brown in 1 hour, a brown color in about 2 hours and very dark brown in 8 hours. At the end of 8 hours, the reaction mixture was sampled and the solution color of the mixture was determined and found to have a color equivalent to APHA 1600. At the end of 10 hours, the APHA color had increased to 2,300. In addition to the product, 51 g. of a nondistillable black tar was obtained.

Example 5 — Hydrochlorination of Pentaerythritol

Example 3 of the Japanese Pat. No. 39-27230 was herein repeated. To 136 g. of pentaerythritol, 5.1 g. (0.05 mole equivalent to pentaerythritol) of acetic anhydride was added and the chlorination was carried out in the manner described in Example 4, above, for 12 hours at 180°–190°C. to yield 63 g. of a residue having a boiling point of 115°–130°C./4–5 mm. Hg. This residue was completely solid and contained a trace of pentaerythritol trichlorohydrin monoacetate. The total HCl fed was 468 g. (12.9 moles). The reaction mixture turned brown within 30 minutes was a dark brown cloudy liquid within 1.5 hours. The mixture was sampled at the end of 8 hours and found to have an APHA color of about 2,500. At the end of 12 hours, the APHA color had increased to greater than 3,000. In addition to the product, 70 g. of a non-distillable black tar was obtained.

Example 6 — Saponification of Tribromoneopentyl Acetate

This example was carried out to show that the production of brominated pentaerythritols via the process of esterification and saponification is not feasible. The reaction stoichiometry would lead one to believe that 1 mole of tribromoneopentyl acetate reacted with 1 mole of sodium hydroxide would yield 1 mole of tribromoneopentyl alcohol plus 1 mole of sodium acetate. This is not the case. In performing this example, the procedure employed was that used in Example 2 of British Pat. No. 764,664.

The reaction was carried out in a 500 ml. round bottomed flask equipped with a mechanical stirrer, a thermometer, a reflux condenser, and a dropping funnel. Pentaerythritol tribromohydrin monoacetate (184 g., 0.5 m.) was charged to the flask and heated to 100°C. A 20% caustic soda solution (20 g. NaOH in 100 ml. $H_2O$) was added and the reaction maintained at 100°C. for 1 hour. At this point, the pH of the aqueous phase had dropped to 7. The reaction mixture was cooled and the phases separated. Titration of the water phase (117 ml.) indicated the presence of 0.36 moles of bromide ion. The organic phase (149 g.) was treated with 10 drops of concentrated aqueous hydrobromic acid. No crystallization occurred. The oil phase was analyzed by G.L.C. and NMR analysis and found to consist principally of pentaerythritol tribromohydrin monoacetate — 69.2%, pentaerythritol tribromohydrin — 13.7%, 3,3-bis(bromomethyl)oxetane — 13.1%, and 2-bromomethyl-3-bromopropene-1 — 3.9%. The yield of pentaerythritol tribromohydrin (tribromoneopentyl alcohol) based on the acetate consumed was 44.5%. Organic recovery was about 90%. Of the original 1.50 gram-atoms of bromine in 0.5 mole of acetate, 0.36 (24%) appeared as bromide ion in the water phase.

Comparative Examples A and B

To show the efficiency of the carboxylic acids as catalysts, Examples A and B were separately prepared in two-liter flasks equipped with a stirrer and a condenser followed by a water scrubber to adsorb any unreacted HBr that passed through the system as follows:

Example A charge was 544 g. of pentaerythritol (4 moles), 350 ml. perchloroethylene and 907 g. anhydrous HBr. The anhydrous HBr was weighed and metered into the reaction continuously over a period of 6.7 hours at 116° to 120°C. with stirring. The HBr fed was a 40% excess over the amount required for di-brom formation. The HBr and perchloroethylene were then stripped off under vacuum to 114°C. at 15 mm. Hg. 545 g. of a white solid was recovered which turned out to be essentially pure pentaerythritol. Titration of the scrubber and distillate gave a total recovery of the HBr charged, indicating no reaction between the HBr and the pentaerythritol.

Example B charge was the same as Example A, above, except that 54 g. of $H_2O$ was also added. The anhydrous HBr (40% excess over the stoichiometric amount needed to obtain a di-brom) was weighed and metered into the reaction over a period of 5.3 hours while heating and stirring at 103° to 120°C. at a constant pressure of 5 p.s.i.g. The HBr, perchloroethylene, water mixture was then stripped off under vacuum to 118°C. at 15 mm. Hg. The product was a soft tan colored material weighing 738 g. which did not change color upon addition of epichlorohydrin. 8.6 moles (out of a total of 11.2 moles) of HBr were recovered. G.L.C. analysis of the product showed very little reaction, giving:

pentaerythritol — 39.8%
mono-brom — 58.0%
di-brom — 8.2%

In the same manner as shown by Examples 1 and 2 above, other aliphatic carboxylic acids, such as propionic acid, butyric acid, hexanoic acid, and octanoic acid, are substituted for the acetic acid and the acid is observed to have a desirable catalytic effect on the reaction. In the same manner, halogenated aliphatic monocarboxylic acids, such as chloroacetic acid, trichloroacetic acid, trifluoroacetic acid, bromoacetic acid, 2,2,3-trichlorobutyric acid, 2,3-dibromopropionic acid and 2-iodohexanoic acid, are employed in place of acetic acid to give a desirable catalytic effect. Also in the same manner as shown for acetic acid, anhydrides, such as acetic anhydride, dichloroacetic anhydride, propionic anhydride and heptanoic anhydride, are used as catalysts in the reaction to obtain similar results. Also, other solvents are employed in the reaction of the invention. For example, water or perchloroethylene as shown in the examples above can be replaced by other solvents such as saturated hydrocarbon solvents like benzene, toluene, xylene, cyclohexane or petroleum ether or chlorinated hydrocarbon solvents like methylene chloride, trichloroethylene, chlorobenzene or hexachlorocyclopentadiene.

We claim:

1. In the process for preparing brominated pentaerythritols by contacting pentaerythritol with HBr, the improvement comprising reacting the pentaerythritol with HBr in the liquid phase at a temperature of from about 85° to about 135°C. in a solvent selected from the groups consisting of benzene, toluene, xylene, a saturated hydrocarbon solvent, a substantially nonreactive brominated or chlorinated hydrocarbon solvent, and water, containing as a catalyst an alkanoic acid of from 2 to 8 carbon atoms or its anhydride having a concentration of from about 0.8 to about 25 mole percent per mole of pentaerythritol, by feeding the HBr to the reactor containing the pentaerythritol and solvent continuously throughout the reaction to saturate the reaction mixture with HBr while retaining in the reaction mixture until completion of the reaction water formed during the reaction and any water used as solvent.

2. The process of claim 1 wherein the catalyst is an alkanoic acid of 2-4 carbons.

3. The process of claim 1 wherein the catalyst is acetic acid.

4. The process of claim 1 wherein the concentration of the alkanoic acid is from about 2 to about 10 mole percent per mole of pentaerythritol.

5. The process of claim 1 wherein the solvent is water or perchloroethylene.

6. The process of claim 1 wherein the temperature is from about 90° to about 120°C.

7. The process of claim 1 wherein the predominant product obtained is dibromoneopentyl glycol.

8. The process of claim 1 wherein the predominant product obtained is tribromoneopentyl alcohol.

9. In the process for preparing brominated pentaerythritols by contacting pentaerythritol with HBr, the improvement comprising reacting the pentaerythritol with HBr in the liquid phase at a temperature of from about 85° to about 135°C. in a solvent selected from the group consisting of water and perchloroethylene, containing as a catalyst acetic acid or its anhydride having a concentration of from about 0.8 to about 25 mole percent per mole of pentaerythritol, by feeding the HBr to the reactor containing the pentaerythritol and the solvent continuously throughout the reaction to saturate the reaction mixture with HBr while retaining in the reaction mixture until completion of the reaction water formed during the reaction and any water used as solvent.

* * * * *